United States Patent [19]

Arena et al.

[11] Patent Number: 4,734,366

[45] Date of Patent: Mar. 29, 1988

[54] BIOLOGICAL PROCESS FOR L-FRUCTOSE SYNTHESIS

[75] Inventors: Blaise J. Arena, Des Plaines; Albrecht H. Bruckner, Palatine, both of Ill.

[73] Assignee: UOP Inc., Des Plaines, Ill.

[21] Appl. No.: 693,567

[22] Filed: Jan. 22, 1985

[51] Int. Cl.$^4$ .................. C12N 9/04; C12P 19/02; C12R 1/01; C12R 1/02
[52] U.S. Cl. .................... 435/105; 435/190; 435/822; 435/823
[58] Field of Search ............... 435/105, 190, 822, 823

[56] References Cited

U.S. PATENT DOCUMENTS

| | | | |
|---|---|---|---|
| 4,207,413 | 6/1980 | Szarek et al. | 536/1 |
| 4,262,032 | 4/1981 | Levin | 426/658 |
| 4,371,616 | 2/1983 | Huibers | 435/105 |
| 4,421,568 | 12/1983 | Huibers | 127/48 |
| 4,440,855 | 4/1984 | Horwath et al. | 435/105 |
| 4,467,033 | 8/1984 | Horwath et al. | 435/105 |

*Primary Examiner*—Elizabeth Weimar
*Attorney, Agent, or Firm*—Thomas K. McBride; John F. Spears, Jr.; Eugene I. Snyder

[57] ABSTRACT

L-fructose may be made by oxidziing L-mannitol with a polyoldehydrogenase from species of the genus Gluconobacter and Acetobacter. In particular, L-fructose may be formed by fermentation of L-mannitol using *Gluconobacter oxydans* ssp. *suboxydans* or *Acetobacter pasteurianus*.

6 Claims, No Drawings

BIOLOGICAL PROCESS FOR L-FRUCTOSE SYNTHESIS

BACKGROUND OF THE INVENTION

Present dietetic needs, predilections, and perceptions have led to the increased use of artificial sweeteners as a replacement for the "natural" sugars, including sucrose and fructose. Such artificial sweeteners are highly imperfect, including being under continual review for their long term physiological effects, yet their demand has grown unabated. Accompanying their growth as a commercial area with substantial economic impact has been a renewed emphasis on discovering and supplying new artificial sweeteners. Recently the class of L-sugars has been actively explored as a source of new sweeteners, with particular emphasis on L-fructose.

Exploitation of the favorable properties of L-sugars is hindered by their relative unavailability. L-fructose, for example, is not found to any significant extent in nature. This unavailability has spurred recent efforts in developing commercially feasible methods for preparing L-sugars in amounts necessary for their use as a staple of commerce. U.S. Pat. Nos. 4,371,616 and 4,421,568 describe a method of producing L-sugars, including L-idose and L-glucose, from the readily available D-glucose. Although the preparation of a number of L-sugars is described in U.S. Pat. No. 4,262,032 the focus seems to be on typical laboratory methods wholly unsuited for economical industrial production, in contrast to the process herein. U.S. Pat. No. 4,440,855 uses glucose oxidase to convert L-glucose to L-glucosone. To the extent that there are suitable procedures adaptable to the large scale production of L-glucose as well as the conversion of L-glucosone to L-fructose, the teachings of the patentee relate to the preparation of L-fructose. The subject matter of U.S. Pat. No. 4,207,413 is L-sucrose, the enantiomer of ordinary table sugar, which can be hydrolyzed to afford L-fructose. More recently U.S. Pat. No. 4,467,033 described the oxidation of L-sorbitol to L-fructose using D-iditol dehydrogenase from certain mutants of the genus Pseudomonas.

The oxidation of D-mannitol to D-fructose using a polyoldehydrogenase is a known process. However, the analogous conversion of L-mannitol to L-fructose has not been described, no doubt because bacterial enzyme systems are constructed to operate largely, if not exclusively, on the naturally occurring D-sugars. It is unclear from the prior art whether a suitable polyoldehydrogenase for L-mannitol oxidation exists, and even if it does the art gives no hint where to find such an enzyme. We have now discovered that species of the genera Gluconobacter and Acetobacter produce a polyoldehydrogenase which readily converts L-mannitol to L-fructose, a discovery leading to our invention which is a method of making L-fructose by oxidizing L-mannitol with said enzyme.

Just as the discovery of an enzyme which converts L-mannitol to L-fructose is a novel departure from the prior art, so is the use of L-mannitol as the source of L-fructose. Although L-sorbitol may be enzymatically oxidized to L-fructose as described above, the instant process is highly advantageous where L-mannitol is the more readily available L-hexitol, or where L-mannitol or a precursor is produced as an otherwise indesirable byproduct.

SUMMARY OF THE INVENTION

The object of this invention is the preparation of L-fructose by a biological method. An embodiment is the oxidation of L-mannitol using a polyoldehydrogenase from species of the genus Gluconobacter or Acetobacter. In a more specific embodiment the enzyme is from *Gluconobacter oxydans* ssp. *suboxydans* or *Acetobacter pasteurianus*.

DESCRIPTION OF THE INVENTION

The invention herein is a method of making L-fructose comprising oxidizing L-mannitol with a polyoldehydrogenase from species of the genus Gluconobacter or Acetobacter, and recovering the L-fructose produced thereby. This process is based on the discovery that many species of the genera Gluconobacter or Acetobacter produce a dehydrogenase which ozidizes L-mannitol to L-fructose.

It is to be emphasized that many species of Gluconobacter and Acetobacter produce a polyoldehydrogenase effecting the desired oxidation. While this is not to say that all species of these genera produce such an enzyme, yet it is important to realize that producing species are readily recognized and identified. In particular, the determination of operative species can be made relatively simply by culturing microorganisms in a medium containing L-mannitol and analyzing for L-fructose formation. Many such methods can be devisd by one skilled in the art, and such methods are exemplified by the one described in U.S. Pat. No. 4,467,033. Among species of Gluconobacter which may be used in the practice of this invention is included *G. oxydans* subspecies *suboxydans*. Among the Acetobacter species are included *A. pasteurianus* and *A. aceti*, especially ssp. *xylinum*. Other microorganisms which may be used in the practice of this invention, but not necessarily with equivalent results, are *Azomonas agilis, Cellvibrio polyoltrophicus,* and *Pseudomonas fluorescens*.

The source of L-mannitol used in practice of this invention is in no way connected to the success of the instant process. L-mannitol can, perhaps, be most conveniently formed by reduction of L-mannose, which in turn can be produced by several means well known in the art. Since the preparation of L-mannitol is not a part of this invention and can be readily determined by the skilled worker it will not be discussed further.

L-fructose is formed by oxidation of L-mannitol using a polyoldehydrogenase from one of the aforementioned microoragnisms. In one variant the oxidation may be performed using a soluble enzyme. That is, a solution of L-mannitol and a soluble enzyme preparation of a polyoldehydrogenase may be contacted under oxidizing conditions for a time sufficient to form L-fructose. Alternatively, the purified polydehydrogenase, an enzyme preparation containing the polyoldehydrogenase, or polyoldehydrogenase-producing whole cells may be immobilized on a suitable support matrix and a feedstock containing L-mannitol may be passed through a bed of the immobilized polydehydrogenase at a space velocity sufficient to convert all, or a substantial fraction, of L-mannitol to L-fructose. In yet another variation the L-fructose may be formed from L-mannitol by growing a polyoldehydrogenase-producing species of Gluconobacter or Acetobacter in a medium containing L-mannitol as a carbon source together with an assimilable source of nitrogen and mineral nutrients. As will be recognized, this is a classical fermentation method which, because of the growth requirements of the microorganisms, generally will be performed at a temperature between about 20° and about 50° C. It should be emphasized that L-mannitol need not be the sole carbon source for microorganism growth; however desirable it may be to have L-mannitol as the sole carbon source, it often is unattainable simply because of the unavailability of pure L-mannitol. Where such limitations are present, L-mannitol need be only part of the carbon source, the major effect of other carbon sources being to complicate somewhat the subsequent recovery of the L-fructose formed during fermentation.

It should be mentioned that not all microorganisms producing a polyoldehydrogenase capable of effecting the L-mannitol to L-fructose conversion may be able to utilize L-mannitol for growth. Therefore, the growth medium need not include L-mannitol, whereas the "fermentation" medium must contain it. The term "fermentation" in this context is meant only to denote a process for conversion of some substrate present in the medium by a microorganism present in the fermentation broth, irrespective of growth or non-growth of the microorganism.

Whichever process variation is used, the L-fructose formed in the oxidation of L-mannitol is then recovered by suitable means. For example, where L-fructose is formed via an immobilized polyoldehydrogenase the effluent is collected and the L-fructose separated from any salts by, for example, ion exchange chromatography, and the fructose then separated from reactant L-mannitol and other materials which may be present in the feedstock by chromatographic methods. In the case of L-fructose production by fermentation a more elaborate separation scheme may be necessary. Such a scheme could use a combination of ion exchange chromatography, precipitation with phenylhydrazine, membrane separation, adsorption chromatography separation, and so forth. It will be appreciated by the practitioner that the particular mode of separation chosen does not influence the success of the invention.

The example given below is merely illustrative of this invention and is not intended to limit it thereby.

EXAMPLE

An aqueous solution (132 g) containing 5.8 wt. % L-glucose and 10.9% L-mannose was hydrogenated in a sealed rotating autoclave at 2000 psig hydrogen at 100° C. for 4 hours using as a catalyst 3.1 g of 1% ruthenium dispersed on carbon. After the reduced mixture was cooled, catalyst was removed from the product by filtration. The filtrate was concentrated by evaporation under vacuum at 50° C. to approximately onehalf of its original volume, at which point a precipitate formed. This precipitate was washed with methanol and was recrystallized twice more from water to yield 2.2 g of material composed of 89.9% L-mannitol, 7.8% L-sorbitol and 2.3% unknown.

The conversion of L-mannitol to L-fructose by fermentation can be accomplished using such microorganisms as *Gluconobacter oxydans* ssp. *suboxydans,* ATCC 23777, and *Acetobacter pasteurianus,* ATCC 23767. The procedure to produce L-fructose by these bacteria consists of two steps, the preparation of cells followed by fermentation.

Preparation of Cells

Sufficient amounts of active bacterial cells containing polyoldehydrogenases catalyzing the oxidation of alditols to ketoses were prepared by growth of the bacteria in a liquid medium. The liquid medium contained 0.5% yeast extract, 0.05% $KH_2PO_4$ and 1% of glycerol as source of carbon and energy. Sorbitol or other sources of carbon may also be used. The pH of the medium was pH 6.5. 50 ml of the medium were transferred in shake flasks (total volume of 250 ml) and sterilized by autoclaving. The flasks were inoculated with bacteria from agar-slants. The solid medium for these slants contained 0.5% yeast extract, 0.3% peptone, 2% glycerol or sorbitol, and 1.5% agar. After inoculation, the flasks were incubated on a shaker at 200 rpm and 30° C. for about 18-24 hours to obtain actively growing cells giving an optical density of OD=2-3 (at 1 cm and 650 nm). The cells were harvested by sterile centrifugation and the cell pellet was washed and centrifuged again with a sterile medium of the composition cited above, but without glycerol, sorbitol, or any utilizable carbon source. The washed cells were resuspended in the medium containing 0.5% yeast extract, 0.05% $KH_2PO_4$, and 1% L-mannitol.

Fermentation

Aliquots of the cell suspension were used to inoculate sterile shake flasks which contain a liquid medium havng the following composition: 0.5% yeast extract, 0.05% $KH_2PO_4$ and 1% L-mannitol at a pH of 6.5. The optical density of the inoculated flasks should be OD=0.5-2.0 (at 1 cm and 650 nm). The fermentation of L-mannitol was carried out for a period of time sufficient to convert L-mannitol to L-fructose, generally for 1 to 2 days, with a shaker speed of 200 rpm and at 30° C. The optimal fermentation time may be determined by analysis of several samples taken at various time points and quantitation of the L-fructose by HPLC. At the end of the fermentation, the cells were separated from the L-fructose containing broth by centrifugation, and L-fructose may be obtained from the liquid by known techniques, e.g., ion-exchange, phenylhydrazine treatment, or other chemical separation and isolation steps.

What is claimed is:

1. A method of making L-fructose comprising oxidizing L-mannitol with a polyoldehydrogenase from species of the genus Gluconobacter or Acetobacter, and recovering the L-fructose produced thereby.

2. The method of claim 1 where the polyoldehydrogenase is from *Gluconobacter oxydans* subspecies *suboxydans.*

3. The method of claim 1 where the polyoldehydrogenase is from *Acetobacter pasteurianus.*

4. A method of making L-fructose from L-mannose comprising oxidizing L-mannitol by polyoldehydrogenase-producing species of the genus Gluconobacter or Acetobacter in a medium containing L-mannitol as a carbon source and an assimilable source of nitrogen and mineral nutrients at a temperature from about 20° to about 50° C., and recovering the L-fructose produced thereby.

5. The method of claim 4 where the microorganism is *Gluconobacter oxydans* subspecies *suboxydans.*

6. The method of claim 4 where the microorganism is *Acetobacter pasteurianus.*

* * * * *